United States Patent [19]
Hoy

[11] Patent Number: 5,472,409
[45] Date of Patent: Dec. 5, 1995

[54] ADJUSTABLE BRACE

[76] Inventor: David J. Hoy, 1270 Rosedale Dr., Mansfield, Ohio 44906

[21] Appl. No.: 311,417

[22] Filed: Sep. 23, 1994

[51] Int. Cl.⁶ .................................................. A61F 5/00
[52] U.S. Cl. ............................ 602/5; 602/12; 602/20; 602/26
[58] Field of Search ................................. 602/5, 12, 16, 602/20, 26; 623/24, 25, 26

[56] References Cited

U.S. PATENT DOCUMENTS

| | | | |
|---|---|---|---|
| 401,933 | 4/1889 | Camp | 602/16 |
| 1,072,369 | 9/1913 | Spahn | 602/16 |
| 4,214,577 | 7/1980 | Hoy | 602/16 |
| 4,801,138 | 1/1989 | Airy et al. | 602/26 |
| 5,052,379 | 1/1991 | Airy et al. | 602/16 |
| 5,108,455 | 4/1992 | Telikicherla | 623/33 |
| 5,302,169 | 4/1994 | Taylor | 602/16 |

*Primary Examiner*—Richard J. Apley
*Assistant Examiner*—Kim M. Lee
*Attorney, Agent, or Firm*—Woodling, Krost & Rust

[57] ABSTRACT

An adjustable brace including a trilateral center segment, a first end segment and a second end segment. The first and second end segments include first and second springs respectively. The first and second springs are affixed to the first and second end segments. The first and second springs enable adjustment of the first and second end segments with respect to the trilateral center segment. Each of the end segments also includes channel means to prevent parallel separation of the end segments from the trilateral center segment.

20 Claims, 8 Drawing Sheets

ADJUSTABLE BRACE

THE FIELD OF THE INVENTION

This invention relates to braces used on human limbs. In particular the invention relates to braces that are used to support the thigh and the calf of a human leg. The adjustable brace comfortably fits and supports the leg of the user. The adjustable brace of the present invention is typically supported by support members extending upwardly from an orthopedic shoe worn by the adjustable brace user. Typically there is a support member on the inside and outside of the user's leg.

BACKGROUND OF THE INVENTION

Leg braces have been in use for many years. However, the existing leg braces do not provide for adjustment of the brace with respect to the particular limb that is to be supported. Typically the existing braces are simply semicircular braces having a uniform diameter. Therefore, many different braces must be available to fit persons of different sizes.

If a limb changes size then a new brace would be required. Specifically, if a person is undergoing therapy on his or her leg the dimensions of the leg may change as the person is rehabilitated. This then requires an adjustable brace so that the brace can be adapted to fit the person's changing leg size or muscle characteristics. If a brace is not adjustable a new brace is required. The present invention provides novel springs and end segments which can be adjusted with respect to a trilateral center segment.

OBJECTS OF THE PRESENT INVENTION

It is an object of the present invention to provide an adjustable brace for the support of human limbs. In particular the human leg requires such a brace. The present invention provides for a center segment and two end segments which are adapted to engage the center segment. This is accomplished through the use of a first and second spring. The springs are affixed to their respective end segments by way of rivets. The springs each include a U-shaped notch which enables adjustment of the springs as will be fully described hereinbelow.

It is a further object of the present invention to provide an adjustable brace which conforms to, and supports, a human limb. In particular it conforms to, and supports, a human thigh and a human calf. This is accomplished through use of the instant novel three segment device. The adjustable brace of the present invention has a center segment sometimes called a trilateral center segment and it has first and second end segments which engage the trilateral center segment. The trilateral center segment has three portions: a first lateral portion, a second lateral portion and a joining portion. The first and second lateral portions are affixed to, and adjustable with respect to, the first and second lateral portions respectively.

It is a further object of the present invention to provide an adjustable brace having first and second springs which conform naturally to the contours of the human leg. It will be obvious to those skilled in the art that the present invention as disclosed would typically include a covering which can be placed over the adjustable brace so as to provide a cushion between the brace and the limb that is being supported. Further, it will be obvious to those skilled in the art that the adjustable brace of the present invention is itself supported by another orthopedic device typically an orthopedic shoe brace.

BRIEF DESCRIPTION OF THE DRAWINGS

The structure operation and advantages of the preferred embodiment of the present invention will become further apparent upon consideration of the following description taken in conjunction with the accompanying drawings, wherein:

FIG. 1 shows the trilateral center segment and the first and second end segments affixed thereto by channel means and by means of the first and second springs.

FIG. 2 shows some of the slots located in the first and second lateral portions of the trilateral center segment.

FIG. 3 shows the first spring as well as the first retaining prong, one of the first adjusting prongs, and the first adjusting tab. FIG. 3 also shows the first upper channel of the first end segment.

FIG. 4 shows the first spring having a U-shaped notch therein. FIG. 4 also shows the first spring riveted to the first end segment. Also shown in FIG. 4 are the retaining prong, the adjusting prongs and the adjusting tab.

FIG. 5 is the reciprocal of FIG. 4. FIG. 5 is identical to FIG. 4 except in regard to the orientation of the components.

FIG. 6 additionally shows the unique contour of the first and second springs. This contour approximates the contour of human limbs. Additionally FIG. 6 shows the angular orientation of the first and second lateral portions of the trilateral center segment with respect to the joining portion of the center segment.

FIG. 7 shows the second spring as well as the second retaining prong, one of the second adjusting prongs, and the first adjusting tab.

DETAILED DESCRIPTION OF THE INVENTION

Figure 1:
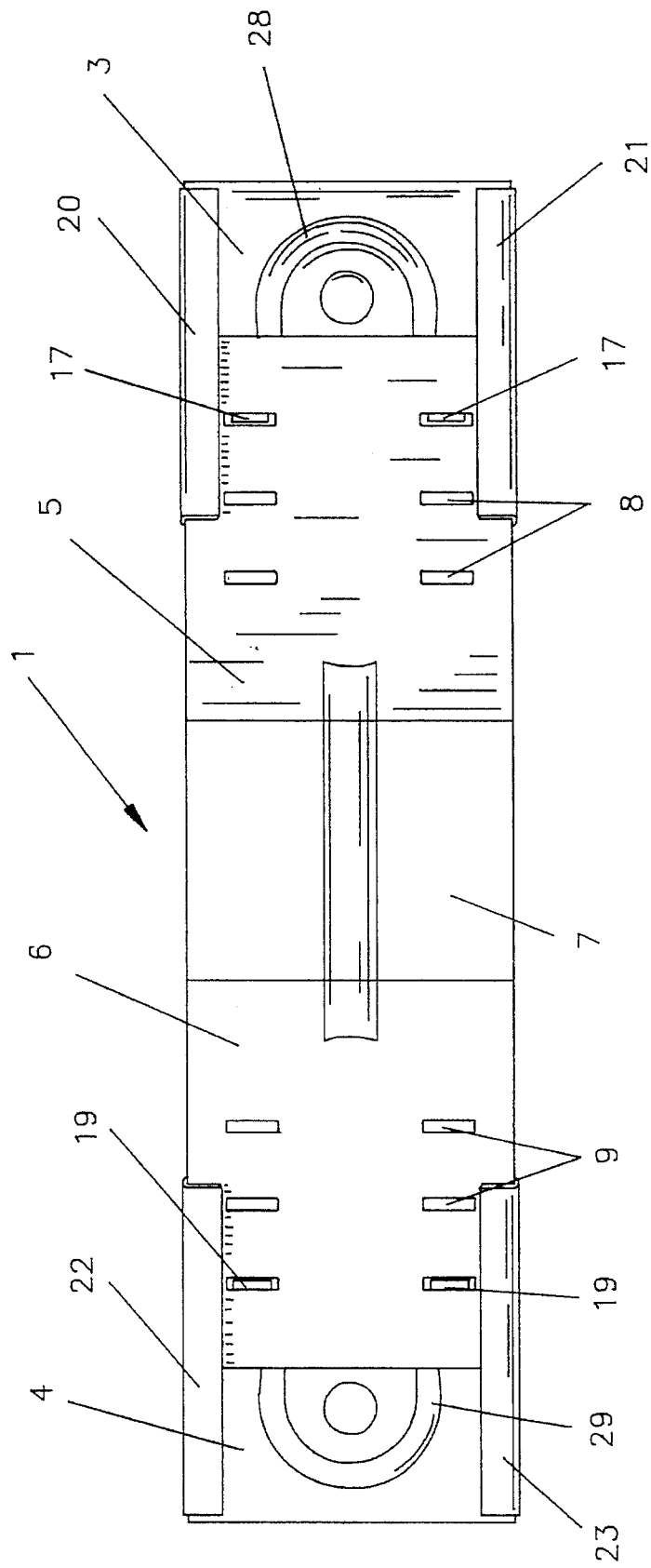
FIG. 1 is a back side view of the adjustable brace.

The adjustable brace of the present invention includes a trilateral center segment 2, a first end segment 3 and a second end segment 4. The trilateral center segment 2 includes a first lateral portion 5 and second lateral portion 6 and a joining portion 7. In the preferred embodiment the first lateral portion, the second lateral portion and the joining portion are all one piece. The joining portion 7 connects the first and second lateral portions thereto.

The first 5 and second 6 lateral portions of the trilateral center segment 2 form obtuse angles with respect to the joining portion 7. It will be understood by those skilled in the art that the angle depicted in the accompanying drawings between the first and second lateral portions and the joining portion is exemplary only. Many different angles could be employed without deviating from the spirit and scope of the instant invention. Additionally, the relative dimensions of the first and second lateral portions, the joining portion, and the first and second end segments can be significantly different without deviating from the spirit and scope of the instant invention.

Figure 2:
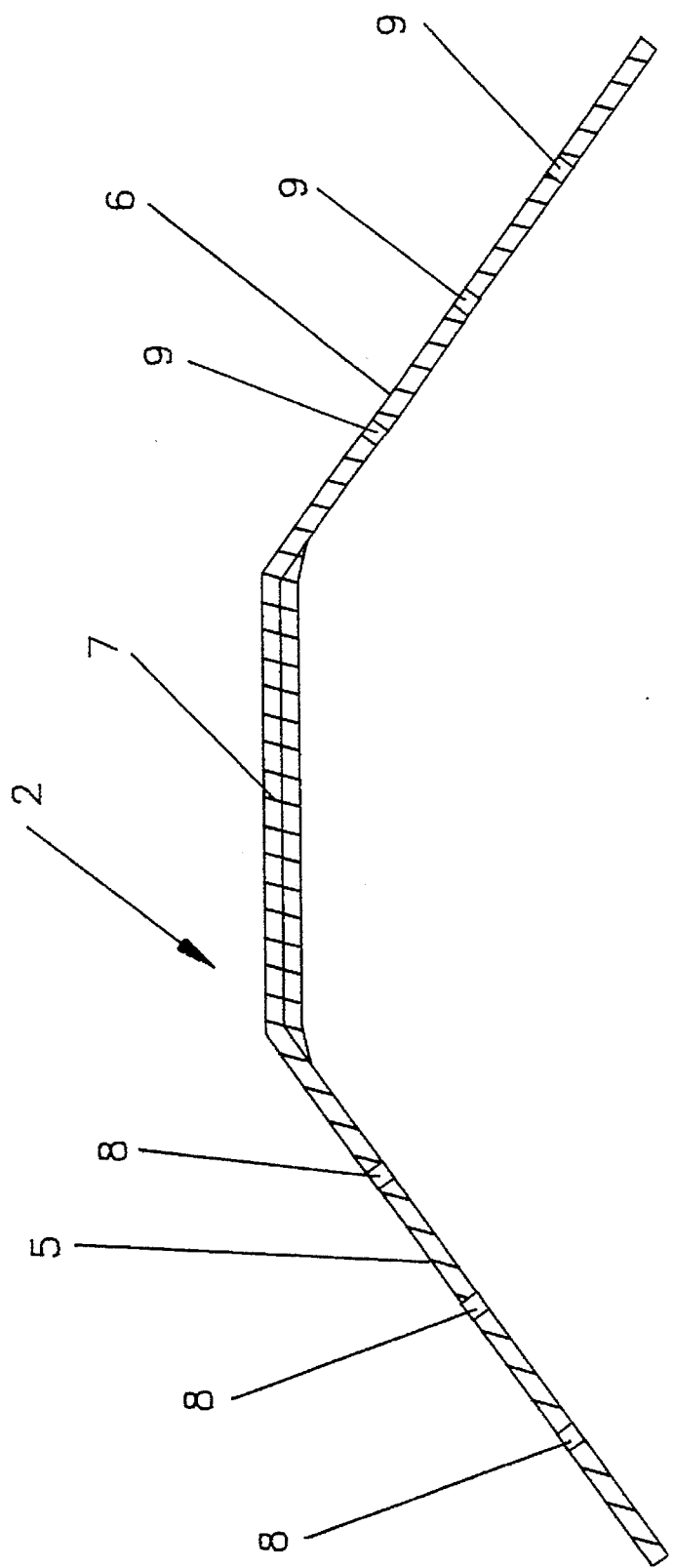
FIG. 2 is a cross-sectional view of the trilateral center segment.

The first lateral portion includes a plurality of first apertures 8 therein. The second lateral portion includes a plurality of second apertures 9 therein. See, FIGS. 1 and 2. These apertures can best seen in FIG. 1. It will be observed that the apertures as illustrated in FIG. 1 are in parallel rows or columns. It will be understood by those skilled in the art that the apertures need not necessarily be arranged in parallel rows or columns. In fact, the adjustable brace would work quite well with just a singular row of apertures in the first and second lateral portions.

Figure 3:
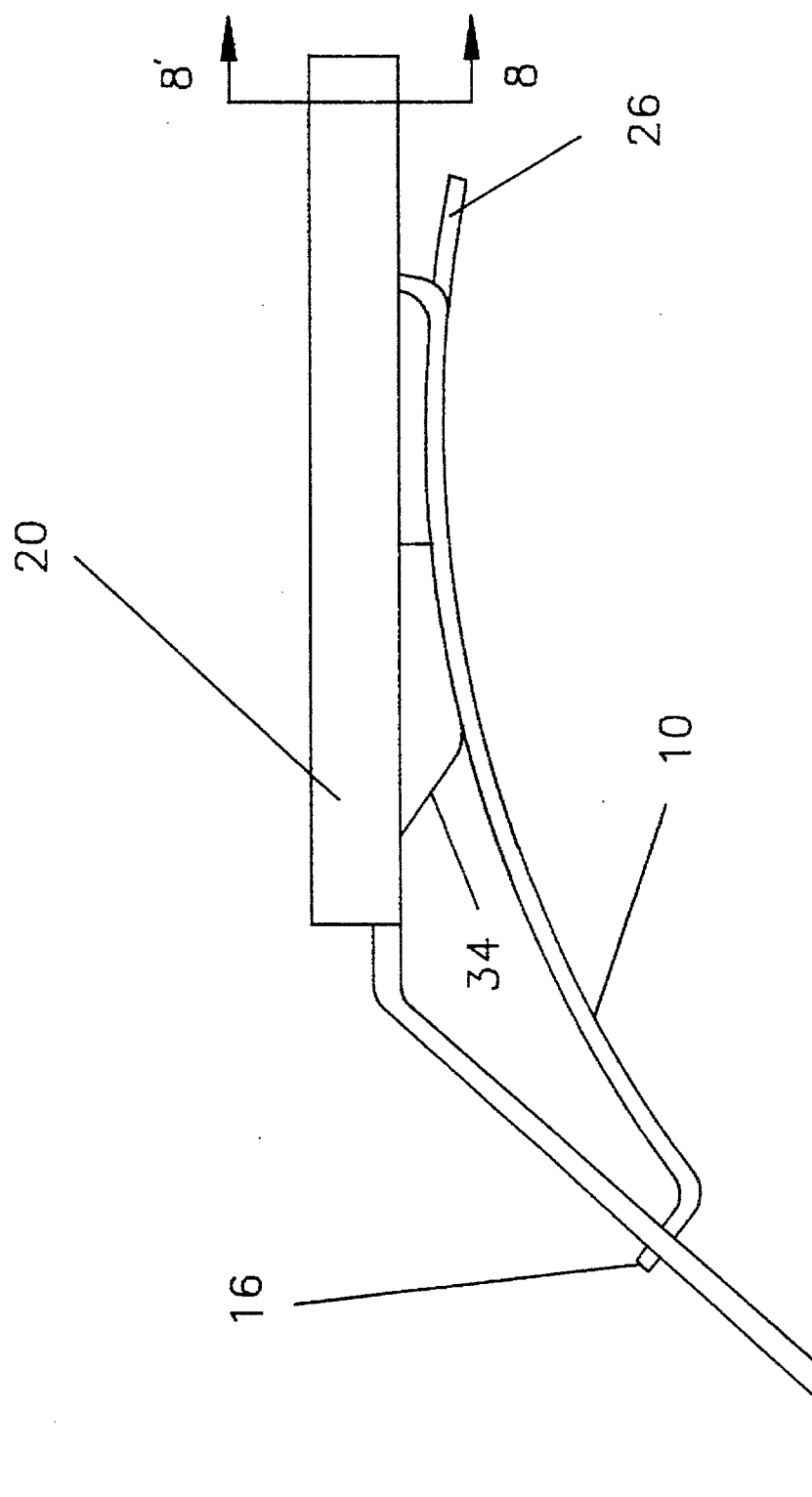
FIG. 3 is an enlarged top view of the first end segment.
Figure 4:
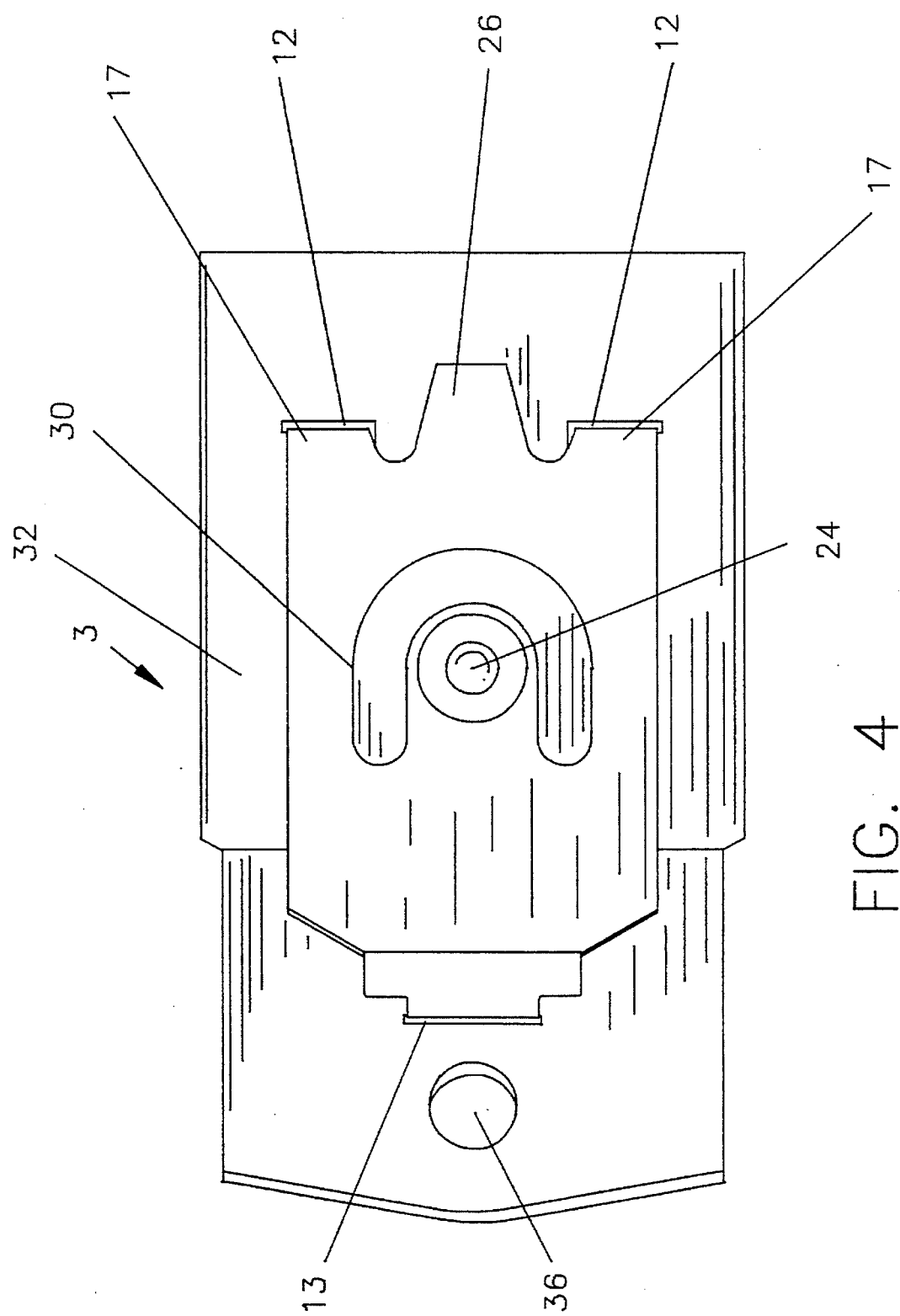
FIG. 4 is an enlarged front view of the first end segment.
Figure 6:
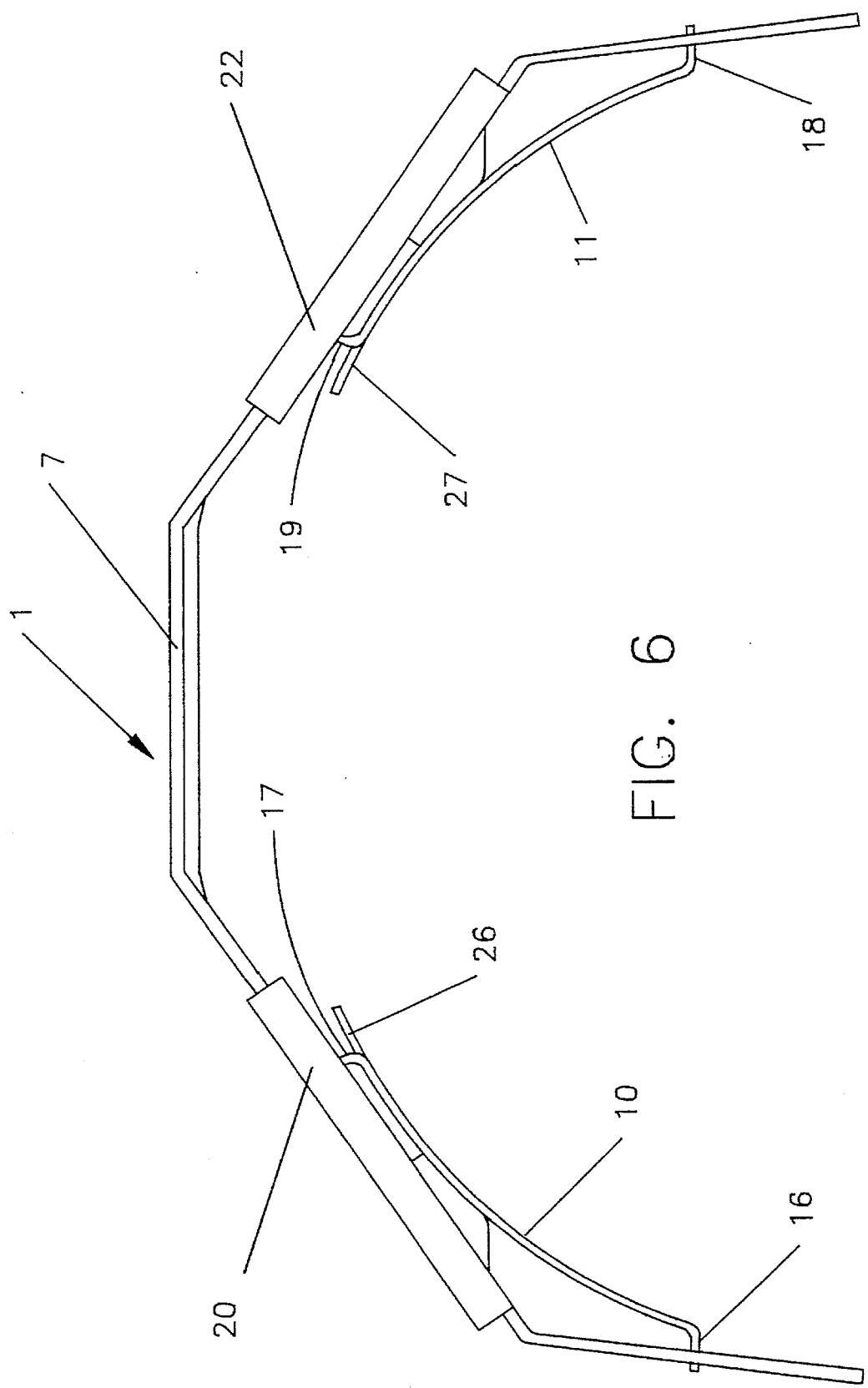
FIG. 6 is a top view of the present invention showing the center segment, the first end segment and the second end segment.

The first end segment includes a first body 32 and a first upper channel 20 and a first lower channel 21. The first end segment 3 has a first spring 10. FIGS. 3, 4 and 6 illustrate the first spring 10. The first spring 10 is affixed to the body 32 of the first end segment 3 by means of a first rivet 24. The first end segment 3 includes a first detent 28. See, FIG. 1. FIGS. 3 and 6 illustrate a convex surface 34 of the first body 32 of the first end segment 3. Convex surface 34 is the opposite side of body 32 where the first detent 28 is located. The first rivet 24 resides in the first detent and affixes spring 10 to the body 32 of the first end segment.

The first detent provides a recess for the first rivet. The first detent permits the first end segment 3 to adjustably move along the first lateral portion 5 of the trilateral center segment 2 during adjustment of the first end segment. The first upper and lower channels prevent parallel separation of the first end segment from the first lateral portion of the center segment.

Figure 7:
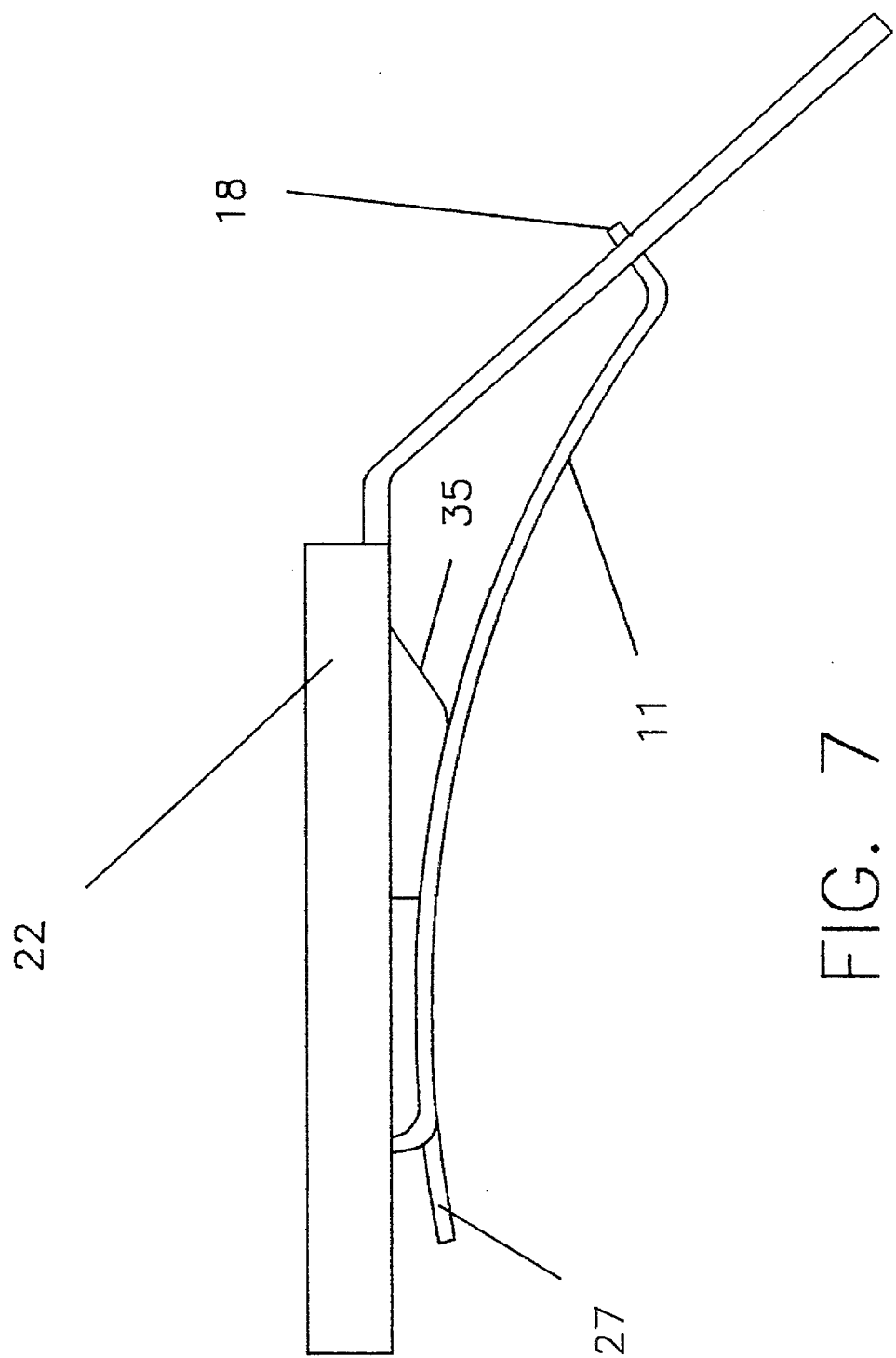
FIG. 7 is an enlarged top view of the second end segment.

The second end segment 4 has a second body 33 and a second upper channel 22 and a second lower channel 23. The second end segment 33 has a second detent 29. See, FIG. 1. FIGS. 6 and 7 illustrate a convex surface 35 of the second body 33 of the second end segment. Convex surface 35 is the opposite side of body 33 where the second detent 29 is located. The second end segment includes a spring 11 affixed to the body 33 of the second end segment by means of a second rivet 25. The second rivet 25 resides in the second detent 29 of the second end segment. The second rivet 25, therefore, does not interfere with the second end segment 4 as it moves along the second lateral portion 6 of the trilateral center segment during adjustment of the second segment. The second upper and lower channels prevent parallel separation of the second end segment from the second lateral portion of the center segment.

The body 32 of the first end segment 3 includes a plurality of first positioning apertures 12 and a first retaining aperture 13. The first spring 10 includes a first retaining prong 16 and a plurality of adjusting prongs 17. See, FIGS. 3, 4 and 6. The first retaining prong 16 resides in the first retaining aperture 13 of the first end segment 3. The adjusting prongs 17 of first spring 10 reside in positioning apertures 12 of the first end segment 3.

The first spring 10 includes an adjusting tab 26. The first spring 10 as previously stated is affixed to the body 32 of the first end segment 3 by means of a first rivet 24. The first spring includes a U-shaped notch 30 as seen in FIG. 4. The U-shaped notch 30 permits the spring 10 to flex when the tab 26 is raised by a person adjusting the first end segment with respect to the first lateral portion of the trilateral center segment. The adjustment of the device is performed by using a screwdriver or other similar tool by applying pressure on the tab 26 lifting it away from the body 32 of the first end segment 3. The U-shaped notch 30 lessens the rigidity of the spring enabling it to bend sufficiently and raise the adjusting prongs 17 slightly.

Figure 5:
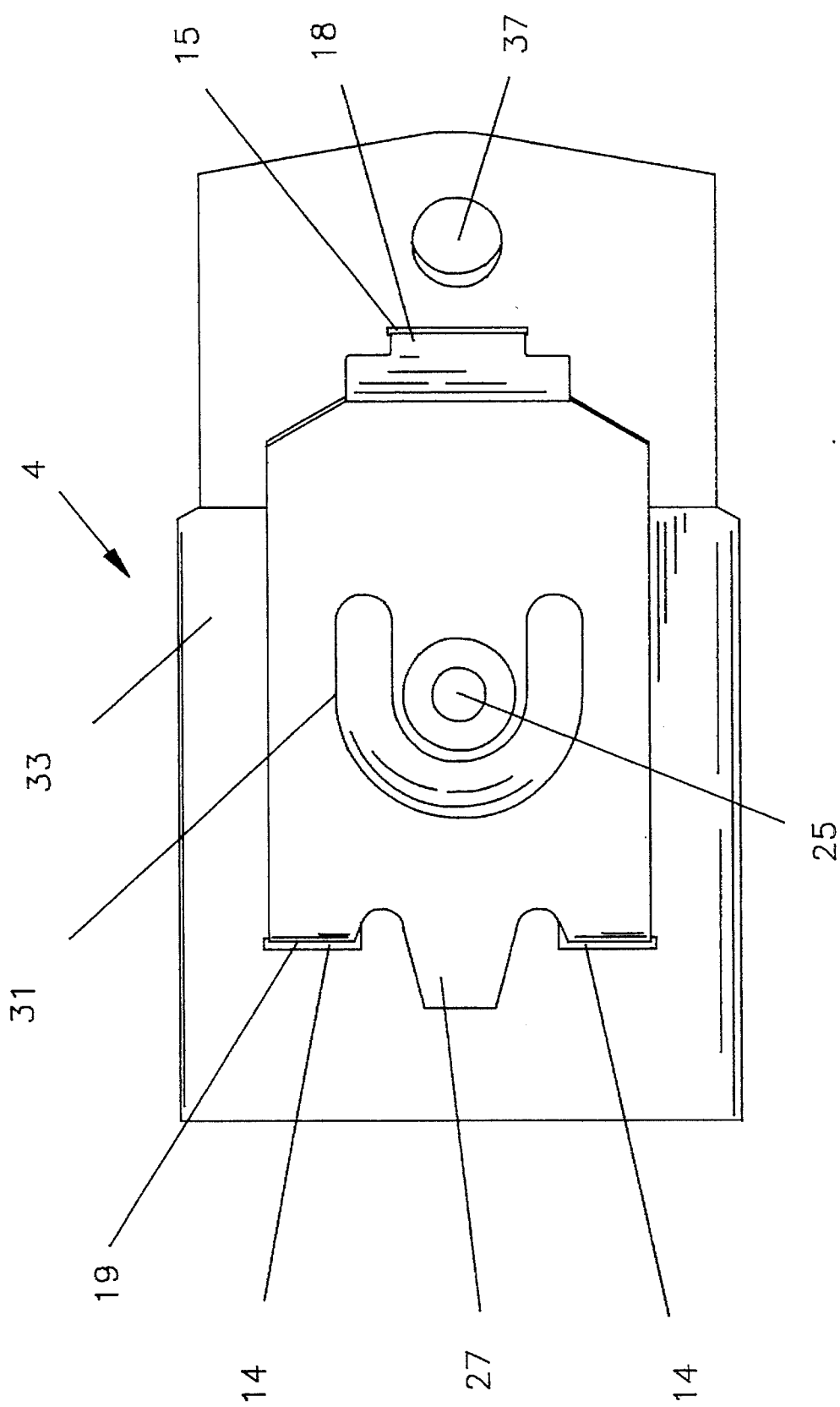
FIG. 5 is an enlarged front view of the second end segment.

The second spring 11 includes an adjusting tab 27. The second spring 11 is affixed to the body 33 of the second end segment 4 by means of a second rivet 25. The second spring includes a U-shaped notch 31 as seen in FIG. 5. The U-shaped notch 31 permits the spring 11 to flex when the tab 27 is raised by a person adjusting the second end segment with respect to the second lateral portion of the trilateral center segment. The adjustment of the device is performed by using a screwdriver or other similar tool by applying pressure on the tab 27 lifting it away from the body 33 of the end segment. The U-shaped notch 31 lessens the rigidity of the spring 11 enabling it to bend sufficiently and raise the adjusting prongs.

Figure 8:
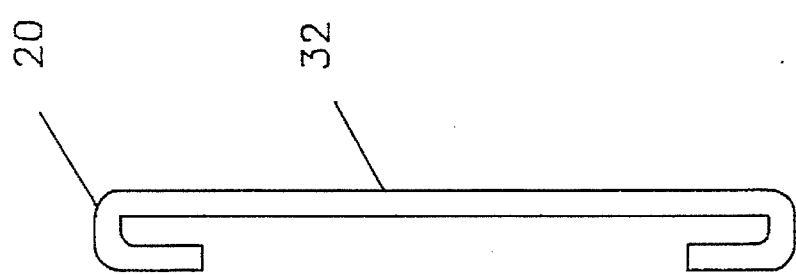
FIG. 8 is a sectional view of the body of the first end segment taken along the line 8—8.

The first and second end segments (3, 4) are designed to slide over the first lateral portion 5 and the second lateral portion 6 of the trilateral center segments. The channels which enable the first and second segments to move are illustrated in FIGS. 1, 3, 6 and 7. FIGS. 1 and 8 are the best illustration of the channels showing the first upper channel 20 and the first lower channel 21 of the first end segment 3 and the second upper channel 22 and the second lower channel 23 of the second end segment 4. Movement of the first and second end segments with respect to the trilateral center segment changes the size of the brace. This enables the brace to fit more people than conventional non-adjustable braces. Additionally, one brace is able to be used and adjusted as the needs change for a given leg or muscle. The brace as shown in FIG. 1 is adjustable to three different positions as illustrated by the columns of the first apertures 8 of the first lateral portion of the trilateral center segment and the apertures 9 of the second lateral portion of the trilateral center segment. However, it would be understood by those skilled in the art that there could be more and/or different positions of the first and second apertures allowing an infinite number of size adjustments of the brace.

With respect to the first end segment 3 and the second end segment 4 it will be observed that the retaining prongs 16 and 18 respectively reside in the retaining apertures (13, 15) and are not moved therefrom during adjustment of the first and second end segments with respect to the trilateral center segment.

The first and second end segments are adjustably positioned with respect to the center segment through the manipulation of the first adjusting tab 26 and the second adjusting tab 27, respectively.

FIG. 1 illustrates the adjusting prongs 17 and 19 residing in the first apertures 8 and the second apertures 9 of the first and second lateral portions of the center segment. FIG. 1 also illustrates the first upper and lower channels (20, 21) enveloping the first lateral portion 5 of the trilateral center segment. FIG. 1 also illustrates the second upper and lower channels (22, 23) enveloping the second lateral portion of the center segment. FIG. 8 illustrates a sectional view of the channel. The adjusting prongs in combination with the channels securely maintain the first and second end segments in place with respect to the center segment.

Upward pressure on an adjusting tab causes the respective adjusting prong 17 or 19 to be retracted and to exit the respective apertures 8, 9 of the center segment allowing the respective body 32, 33 of the first end segment to slide along the respective first or second lateral portion of the center segment. The adjusting prongs 17, 19 do not have to exit the first and second positioning apertures 12, 14 of the first and second end segments during manipulation of adjusting tabs 26, 27. When the respective first or second end segments is positioned with respect to the plurality of respective first or second apertures in the respective first and second lateral portions of the center segment, the pressure is then relieved from the respective tab 26, 27 allowing the adjusting prongs 17, 19 to then engage the plurality of apertures in the first or second lateral portions of the center segment. It will be observed that one of the end segments is adjusted at a time. The adjustment can be done with a simple screwdriver or other metal object sufficiently strong to apply pressure to the tabs 26 and 27. The brace of the present invention is easy to adjust. The braces will also be economical to the patients that wear them in that the brace can be adjusted to meet their changing needs.

The upper and lower channels of the first and second end segments prevent parallel separation of the first and second end segments from the first and second lateral portions of the center segment. The adjusting prongs 17 and 19 of the first and second springs 10 and 11 respectively prevent relative movement of the first and second end segments with respect to the first and second lateral portions of the center segment.

The adjustable brace 1 of the present invention is positioned and supported by support members (not shown) which are rigidly affixed to the first and second segments. First end segment 3 includes a first supporting aperture 36 and second end segment 4 includes a second supporting aperture 37. It will be observed that the first and second end segments could employ many different attachment means for supporting and positioning the adjustable brace.

The preferred embodiment of the present invention employs a trilateral center segment, end segments, springs, and rivets all made of metal. However, it will be obvious to those skilled in the art that the materials are relatively unimportant and that the brace could be constructed of non-metallic materials such as plastic.

While the invention has been described in combination with embodiments thereof, it is evident that many alternatives, modifications and variations will be apparent to those skilled in the art in light of the foregoing description. Accordingly, it is intended to embrace all such alternatives, modifications and variations that fall within the spirit and scope of the appended claims.

What is claimed:

1. A brace comprising a trilateral center segment, a first end segment, and a second end segment, said trilateral center segment includes a first planar lateral portion, a second planar lateral portion, and a substantially planar joining portion, said substantially planar joining portion connecting said first and second planar lateral portions, said first and second planar lateral portions forming obtuse angles with respect to said substantially planar joining portion, and, said first and second end segments adjustably engage said trilateral center segment.

2. A brace as claimed in claim 1 wherein said first lateral portion of said trilateral center segment includes a first aperture, and said second lateral portion of said trilateral center segment includes a second aperture.

3. A brace as claimed in claim 2 wherein said first end segment includes a first body and a first spring and said second end segment includes a second body and a second spring, means for affixing said first spring to said first body of said first end segment and means for affixing said second spring to said second body of said second end segment.

4. A brace as claimed in claim 3 wherein said first end segment includes a first positioning aperture and a first retaining aperture, and said second end segment includes a second positioning aperture and a second retaining aperture.

5. A brace as claimed in claim 4 wherein said first spring includes a first retaining prong and a first adjusting prong, and said second spring includes a second retaining prong and a second adjusting prong, said first retaining prong resides in said first retaining aperture of said first end segment and said first adjusting prong resides in said first positioning aperture of said first end segment, said second retaining prong resides in said second retaining aperture of said second end segment and said second adjusting prong resides in said second positioning aperture of said second end segment.

6. A brace as claimed in claim 5 wherein said first end segment includes a first upper channel and a first lower channel, and said second end segment includes a second upper channel and a second lower channel, said first upper and said first lower channels of said first end segment engage said first lateral portion of said trilateral center segment preventing parallel separation therebetween, said second upper and said second lower channels of said second end segment engage said second lateral portion of said trilateral center segment preventing parallel separation therebetween.

7. A brace as claimed in claim 6 wherein said first adjusting prong of said first spring of said first end segment protrudes into said first aperture of said first lateral portion of said trilateral center segment preventing relative movement between said first end segment and said first lateral portion of said trilateral center segment, and wherein said second adjusting prong of said second spring of said second end segment protrudes into said second aperture of said second lateral portion of said trilateral center segment preventing relative movement between said second end segment and said second lateral portion of said trilateral center segment.

8. An adjustable brace comprising a trilateral center segment; a first end segment, and a second end segment, said first end segment having a first spring affixed thereto, said second end segment having a second spring affixed thereto, said trilateral center segment having a first lateral portion, a second lateral portion, and a joining portion, said first spring of said first end segment adapted to engage said first lateral portion of said trilateral center segment and said second spring of said second end segment adapted to engage said second lateral portion of said trilateral center segment.

9. An adjustable brace as claimed in claim 8 wherein: said first lateral portion of said center segment includes a plurality of first apertures and said second lateral portion of said center segment includes a plurality of second apertures; said first spring of said first end segment includes a first adjusting prong; said second spring of said second end segment includes a second adjusting prong; and said first adjusting prong resides in one of said first apertures of said first lateral portion of said trilateral center segment and said second adjusting prong resides in one of said second apertures of said second lateral portion of said trilateral center segment.

10. An adjustable brace as claimed in claim 9 wherein said first spring of said first end segment includes a plurality of first adjusting prongs and said second spring of said second end segment includes a plurality of second adjusting prongs; said plurality of said first adjusting prongs reside in a plurality of said first apertures of said first lateral portion of said center segment; and, said plurality of said second adjusting prongs reside in a plurality of said second apertures of said second lateral portion of said center segment.

11. An adjustable brace as claimed in claim 10 further including a first rivet and a second rivet, said first and second rivets affix said first and second spring to said first and second end segments respectively.

12. An adjustable brace as claimed in claim 11 wherein: said first end segment includes a first channel means and said second end segment includes a second channel means; said first and second channel means respectively preventing parallel separation of said first and second end segments from said first and second lateral portions of said trilateral center segment.

13. An adjustable brace as claimed in claim 12 wherein said first spring includes a first adjusting tab and said second spring includes a second adjusting tab enabling adjustment of said first and second end segments respectively.

14. An adjustable brace as claimed in claim 13 wherein said first end segment includes a first detent and said second end segment includes a second detent, said first and second rivets residing in said first and second detents respectively.

15. An adjustable brace as claimed in claim 8 wherein said first and second springs are curved leaf springs adapted to engage a human limb.

16. A brace as claimed in claim 7 wherein said first and second springs are curved leaf springs adapted to engage a human limb.

17. A brace comprising a trilateral center segment, a first end segment and a second end segment, said trilateral center segment includes a first lateral portion, a second lateral portion, and a joining portion, said joining portion connecting said first and second lateral portions, said first and second lateral portions forming obtuse angles with respect to said joining portion, said first and second lateral portions including a plurality of first and second apertures respectively, said first and second end segments including a first and a second body respectively, said first and second end segments including first and second springs respectively, said first and second end segments including a plurality of first and second positioning apertures respectively, said first and second end segments include a first and second retaining aperture respectively, said first and second springs including first and second retaining prongs respectively and a first and second plurality of adjusting prongs, said first and second springs include a first and a second U-shaped notch respectively, said first and second retaining prongs reside in said first and second retaining apertures of said first and second end segments, said first plurality of adjusting prongs and second plurality of adjusting prongs reside in said first plurality of positioning apertures and said second plurality of positioning apertures of said first and second end segments respectively, said first end segment includes a first upper and a first lower channel and said second end segment includes a second upper and a second lower channel, said first upper and said first lower channels of said first end segment engage said first lateral portion of said trilateral center segment preventing parallel separation therebetween, said second upper and said second lower channels of said second end segment engage said second lateral portion of said trilateral center segment preventing parallel separation therebetween, said first plurality of adjusting prongs of said first spring of said first end segment reside in said first plurality of apertures of said first lateral portion of said trilateral center segment preventing relative movement between said first end segment and said first lateral portion of said trilateral segment, said second plurality of adjusting prongs of said second spring of said second end segment resides in said second plurality of apertures of said second lateral portion of said trilateral center segment preventing relative movement between said second end segment and said second lateral portion of said trilateral center segment, said first and second end segments include first and second detents respectively, a first rivet and a second rivet, said first and second rivets reside in said first and second detents, of said first and second end segments respectively, said first and second rivets affix said first and second springs to said first and second end segments respectively, said first spring includes a first adjusting tab and said second spring includes a second adjusting tab enabling adjustment of said first and second end segments with respect to said trilateral center segment and a human limb supported by said brace.

18. An adjustable brace as claimed in claim 15 wherein said first and second springs include a U-shaped notch.

19. A brace as claimed in claim 16 wherein said first and second springs include a U-shaped notch.

20. A brace comprising a center segment, a first end segment and a second end segment, a first spring having a U-shaped notch, said first spring affixed to said first end segment, a second spring having a U-shaped notch, said second spring affixed to said second end segment, and means for adjusting said first and second end segments relative to said center segment.

\* \* \* \* \*